United States Patent [19]

Schmidt et al.

[11] Patent Number: 4,929,794
[45] Date of Patent: May 29, 1990

[54] HYDROTREATMENT-ISOMERIZATION WITHOUT HYDROGEN RECYCLE

[75] Inventors: Robert J. Schmidt; Robert S. Haizmann, both of Rolling Meadows, Ill.

[73] Assignee: UOP, Des Plaines, Ill.

[21] Appl. No.: 292,034

[22] Filed: Dec. 30, 1988

[51] Int. Cl.[5] .................................................. C07C 5/13
[52] U.S. Cl. .................................. 585/737; 208/212; 208/216R; 208/217; 585/748; 585/751
[58] Field of Search ...................... 208/212, 216, 217; 585/737, 748, 751

[56] References Cited

U.S. PATENT DOCUMENTS

| | | | |
|---|---|---|---|
| 2,798,105 | 7/1957 | Heinemann | 260/683.5 |
| 2,906,798 | 9/1959 | Starnes et al. | 260/683.65 |
| 2,993,938 | 7/1961 | Bloch et al. | 260/666 |
| 3,391,220 | 7/1968 | Haensel | 260/683.76 |
| 3,791,960 | 2/1974 | Davies et al. | 208/57 |
| 4,627,910 | 12/1986 | Millman | 208/112 |

*Primary Examiner*—Curtis R. Davis
*Attorney, Agent, or Firm*—Thomas K. McBride; John G. Tolomei

[57] ABSTRACT

A combined process for hydrotreating and isomerizing a $C_4$–$C_7$ feedstock is simplified and made more efficient by the use of a common hydrogen source and low hydrogen to hydrocarbon ratio in both the hydrotreating and isomerization steps of the invention. The method supplies hydrogen to a combined hydrotreatment and isomerization process for the isomerization of a feed stream comprising $C_4$–$C_7$ hydrocarbons. The hydrocarbon feed stream contains sulfur and oxygen contaminants and is combined with a hydrogen-containing stream in an amount that produces a maximum hydrogen to hydrocarbon ratio of 0.9 $stdm^3/m^3$ (50 SCFB). The hydrotreater feed is contacted in a hydrotreater reactor with a catalyst comprising a Group VIB metal and a Group VII metal on an alumina support. Effluent from the hydrotreater passes to a first separator that separates the effluent into a first gas stream comprising hydrogen, hydrogen sulfide and water and a treated stream comprising hydrocarbons having from 4–7 carbon atoms. The first gas stream is rejected from the process. The treated stream is mixed with a second hydrogen-containing stream in a proportion that produces a hydrogen to hydrocarbon ratio of from 0.9 to 1.8 $stdm^3/m^3$ (50 to 100 SCFB) to form an isomerization zone feed. The isomerization feed is contacted in an isomerization reaction zone with an isomerization catalyst comprising alumina having from 0.01 to 0.25 wt. % of platinum and from 2 to 10 wt. % of a chloride component at isomerization conditions. The effluent from the reaction zone enters a stabilizer where it is separated into a product stream of $C_4$–$C_7$ hydrocarbons and a second gas stream which is removed from the process.

The common hydrogen supply source and the low hydrogen to hydrocarbon ratios permit operation of the process without hydrogen recycle facilities between the hydrotreatment and isomerization steps and downstream of the isomerization reactor.

11 Claims, 2 Drawing Sheets

HYDROTREATMENT-ISOMERIZATION WITHOUT HYDROGEN RECYCLE

BACKGROUND OF THE INVENTION

This invention relates generally to the hydrotreatment and isomerization of hydrocarbons. This invention relates more specifically to the supply of hydrogen to a hydrotreatment and isomerization process.

DESCRIPTION OF THE PRIOR ART

Hydrotreatment and isomerization are well known processes for the treatment of hydrocarbons. Hydrotreatment is a common method for the upgrading of feedstocks by the removal of contaminants such as sulfur, oxygen and nitrogen. Isomerization raises the octane value of hydrocarbons by rearranging a molecular structure from straight chain paraffinic hydrocarbons to more highly branched hydrocarbons that generally have a higher octane rating.

High octane gasoline is required for modern gasoline engines. Formerly it was common to accomplish octane number improvement by the use of various lead-containing additives. As lead is phased out of gasoline for environmental reasons, it has become increasingly necessary to rearrange the structure of the hydrocarbons used in gasoline blending in order to achieve high octane ratings.

A gasoline blending pool normally includes $C_4$ and heavier hydrocarbons having boiling points of less than 205° C. (395° F.) at atmospheric pressure. This range of hydrocarbon includes $C_4$–$C_6$ paraffins, $C_7$ isoparaffins and especially the $C_5$ and $C_6$ normal paraffins which have relatively low octane numbers. The $C_4$–$C_6$ hydrocarbons have the greatest susceptibility to octane improvement by lead addition and were formerly upgraded in this manner. Octane improvement can also be obtained by using isomerization to rearrange the structure of the paraffinic hydrocarbons into branch-chained paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branch-chained isoparaffins. Although the $C_6$ and heavier hydrocarbons can be upgraded into aromatics through hydrocyclization, the conversion of $C_6$'s and heavier hydrocarbons to aromatics creates higher density species and increases gas yields with both effects leading to a reduction in liquid volume yields. Therefore, it is common practice to charge at least the $C_6$ paraffins to an isomerization unit to obtain $C_6$ ispoparaffin hydrocarbons. Consequently, octane upgrading can use isomerization to convert $C_7$ and lighter boiling hydrocarbons to higher octane species.

The isomerization of paraffins is a reversible first order reaction. The reaction is limited by thermodynamic equilibrium. The basic types of catalyst systems that are used in effecting the reaction is a hydrochloric acid promoted aluminum chloride system and a supported aluminum chloride catalyst. Either catalyst is very reactive and can generate undesirable side reactions such as disproportionation and cracking. These side reactions not only decrease the product yield but can form olefinic fragments that combine with the catalyst and shorten its life. One commonly practiced method of controlling these undesired reactions has been to carry out the reaction in the presence of hydrogen.

Isomerization processes that carry out the reaction in the presence of a halogenated platinum aluminum catalyst usually use a relatively high hydrogen to hydrocarbon ratio. U.S. Pat. No. 2,798,105 teaches the use of a platinum alumina catalyst in the isomerization of $C_4$–$C_5$ hydrocarbons with minor additions of molecular hydrogen to the reaction mixture and a hydrogen to hydrocarbon mole ratio of from 0.5 to 4. The isomerization of $C_4$–$C_7$ hydrocarbons using a low platinum content alumina catalyst with a halogen component and a minimum 0.17 hydrogen to hydrocarbon mole ratio is shown in U.S. Pat. No. 2,906,798. The addition of a halogen to an isomerization process is demonstrated in U.S. Pat. No. 2,993,938 where a catalyst having an aluminum base and a platinum metal and a halogen incorporated thereon is used as an isomerization catalyst in a reaction that uses a 0.2 to 10 hydrogen to hydrocarbon mole ratio. Other isomerization references that teach the use of halogenated platinum alumina catalyst to isomerize $C_4$–$C_6$ hydrorcabons are U.S. Pat. Nos. 3,391,220 and 3,791,960 which teach a required hydrogen to hydrocarbon mole ratio ranging from 0.1 to 15. Thus, the art of isomerization has long recognized the usefulness of catalyst comprising a platinum group metal and a halogen on an alumina support for the isomerizatin of $C_4$–$C_6$ hydrocarbons. However, it has also been generally accepted that these processes require a relatively high ratio of hydrogen to hydrocarbon in order to obtain satisfactory catalyst life and product yields.

One reason for the use of a high hydrogen to hydrocarbon ratio stems from the high susceptibility of the typical platinum-alumina catalysts to sulfur deactivation. The presence of sulfur concentrations as low as 1 ppm can poison the platinum and lead to at least temporary deactivation of the catalyst. Rapid coking of the catalyst has been experienced in most cases following sulfur deactivation. If left unchecked, the coking will be severe enough to require a complete regeneration of the catalyst. The presence of a large excess of hydrogen will moderate or prevent catalyst deactivation during periods of temporary sulfur deactivation. Even when facilities are provided for the treatment and removal of sulfur, it is inevitable that sulfur contamination will at times cause temporary catalyst deactivation. Therefore, it is common practice to maintain relatively high hydrogen/hydrocarbon ratios in the isomerization zone to ameliorate coking and avoid a full regeneration of the catalyst every time it is temporarily deactivated by sulfur.

Despite the need to maintain high hydrogen to hydrocarbon ratios and their susceptibility to sulfur deactivation, these halogenated platinum-alumina catalysts are generally favored for their high conversion and product yields. However, maintaining a relatively high hydrogen to hydrocarbon ratio adds to the cost and complexity of isomerization processes. Most of these costs are related to the recovery and recycling of the hydrogen to isomerization zone. Very little of the hydrogen that enters the isomerization zone is consumed in the process. Therefore, separation facilities are required to remove the hydrogen from the product effluent leaving the isomerization reaction zone. The recovered hydrogen can be recycled to the isomerization zone to minimize the addition of hydrogen to the process. However, compressor facilities must raise the pressure of the hydrogen gas before it is returned to the isomerization zone.

In addition to the problems caused by sulfur, platinum/aluminum catalysts are also affected by water and oxygenate compounds that can decompose to form water. Water can act to permanently deactivate some of the halogenated platinum/aluminum catalysts by removing high activity chloride from the catalyst and replacing it with inactive aluminum hydroxide. Therefore, water and oxygenates in the feed to an isomerization zone can be tolerated in only very low concentrations. The limitation is generally on the order of 0.1 ppm or less.

It is well known that organo-sulfur and organo-oxygen compounds can be removed from hydrocarbon fractions by the use of hydrotreatment. Hydrotreatment feedstocks containing organo-sulfur compounds, such as mercaptans, sulfides, disulfides and thiophenes, are reacted with hydrogen to produce hydrocarbons and hydrogen sulfides. It is well known that the reaction of the organo-sulfur compounds is accelerated by the presence of catalysts comprising Group VIII metals and Group VIB metals supported on a refractory inorganic oxide. Hydrotreating also removes oxygenate compounds by converting them into lower boiling hydrocarbons and water. The water and hydrogen sulfide are removed in a stabilizer from which a purified hydrocarbon stream is recovered.

The desulfurization and deoxygenation of the hydrocarbons in the hydrotreater is basically a hydrogenation process. In hydrogenation processes, the reaction rate is generally believed to be in proportion to the hydrogen partial pressure. Therefore, conventional hydrotreating processes favor the use of fairly high hydrogen to hydrocarbon ratios.

The use of a high hydrogen to hydrocarbon ratio in the hydrotreating process adds significant cost to its operation. Typically, a high hydrogen to hydrocarbon ratio requires recycle facilities for recovering hydrogen and returning it to the hydrotreatment reactor. When hydrogen is recycled, a recycle compressor, additional heat exchangers and extra cooling capacity are all required and add significant capital and operating expense to the process. The expense of the recycle facilities can be avoided by operating with once through hydrogen. But at high hydrogen to hydrocarbon ratios, once-through hydrogen operation is not economical due to high losses of hydrogen and more importantly, product that would occur without again increasing the size and complexity of the product recovery facilities. U.S. Pat. No. 4,627,910, issued to Millman, teaches the hydrotreatment of light feeds including naphtha with a catalyst comprising a Group VIB metals, phosphorus and cobalt on an alumina support at hydrotreatment conditions including a temperature of from 400°–950° F. and a pressure of from 20 to 6000 psig. The Millman reference teaches that the process requires a minimum hydrogen circulation of 50 SCFB with much higher hydrogen to hydrocarbon circulations of 400 to 10,000 SCFB being preferred.

As previously mentioned, the hydrotreatment is necessary to reduce oxygen and sulfur concentrations to the very low levels that are needed in isomerization feed streams. These levels include sulfur concentrations of less than 0.5 ppm and oxygenate concentrations of less than 0.1 ppm. Achieving such complete conversion of sulfur and oxygenate compounds would generally lead those skilled in the art to believe that a high hydrogen to hydrocarbon ratio would be necessary for this degree of contaminant removal in a reasonable size reactor.

The need to recirculate hydrogen in both the hydrotreating and isomerization processes adds significant cost to the operation and capital expense to obtain a high octane fuel for most feedstocks of $C_4$–$C_7$ hydrocarbons. A combination hydrotreatment and isomerization process that could isomerize $C_4$–$C_7$ hydrocarbons without the need for the recycle of hydrogen in either the hydrotreatment or isomerization process would have significant cost advantages.

Accordingly, it is an object of this invention to provide an isomerization process that uses a halogenated platinum/aluminum catalyst on an alumina support to isomerize a feed stream of $C_4$–$C_7$ hydrocarbons that contain oxygenate and sulfur contaminants without the need for the recycle of hydrogen.

Another object of this invention is the elimination of recycle facilities for maintaining a high hydrogen to hydrocarbon ratio in an isomerization process.

Another object of this invention is the hydrotreatment and isomerization of $C_4$–$C_7$ hydrocarbon feedstock without the use of hydrogen recycle in either the hydrotreatment or isomerization process.

A yet further object of this invention is a hydrotreatment and isomerization process that reduces sulfur and oxygenate contaminants to levels of less than 0.5 ppm and 0.1 ppm, respectively, without the use of a hydrogen recycle

BRIEF DESCRIPTION THE INVENTION

Thus, this invention is a process for hydrotreating a feed stream comprising hydrocarbons having from 4–7 carbon atoms in a hydrotreating reactor that uses a very low concentration of hydrogen to reduce sulfur and oxygenate levels to 0.5 ppm and 0.1 ppm, respectively. The hydrotreatment process of the invention contacts the $C_4$–$C_7$ hydrocarbon feed stream with a catalyst comprising a Group VIB and a Group VIII metal on an alumina support. This hydrotreatment reactor has been found to provide good conversion of sulfur compounds and even oxygenate compounds at very low hydrogen to hydrocarbon ratios. The hydrogen to hydrocarbon ratios are low enough to permit the hydrotreament process to operate without the recycle hydrogen and with ordinary facilities for the separation of hydrogen, $H_2S$ and $H_2O$ from the hydrotreating product. After separation of hydrogen $H_2S$ and $H_2O$, the effluent from the hydrotreatment reactor enters the isomerization zone. The invention uses a highly active chlorided platinum/aluminum catalyst in the isomerization reaction zone which has been discovered to retain its stability with hydrogen levels that are at or only slightly greater than the stoichiometric requirement for the isomerization reaction. The isomerization reaction zone also achieves high conversion and good stability with a very low concentration of hydrogen. The surprising ability of these catalysts to isomerize $C_4$–$C_7$ hydrocarbons over long periods of time without a large excess of hydrogen allows the elimination of a hydrogen recycle system from the process.

Accordingly, in one embodiment, this invention is a method of supplying hydrogen to a combined hydrotreatment and isomerization process for the isomerization of a feed stream comprising $C_4$–$C_7$ hydrocarbons. The hydrocarbon feed stream contains sulfur and oxygen contaminants and is combined with a hydrogen-containing stream in an amount that produces a maximum hydrogen to hydrocarbon ratio of 0.9 stdm³/m³ (50 SCFB). The hydrotreater feed is contacted in a hydrotreater reactor with a catalyst comprising a Group VIB metal and a Group VIII metal on an alumina support. The hydrotreater reactor operates at a temperature in the range of 200°–350° C., a pressure of from 700 to 5600 kPa and a liquid hourly space velocity of from 1 to 20. The hydrotreater reactor converts sulfur and oxygen-containing compounds to hydrocarbons, hydrogen sulfide and water. Effluent from the hydrotreater passes to a first separator that separates the effluent into a first gas stream comprising hydrogen, hydrogen sulfide and water and a treated stream comprising hydrocarbons having from 4–7 carbon atoms. The first gas stream is rejected from the process. The treated stream is mixed with a second hydrogen containing stream in a proportion that produces a hydrogen to hydrocarbon ratio of from 0.9 to 1.8 stdm³/m³ (50 to 100 SCFB) to form an isomerization zone feed. The isomerization feed is contacted in an isomerization reaction zone with an isomerization catalyst comprising alumina having from 0.01 to 0.25 wt.% of platinum and from 2 to 10 wt.% of a chloride component at isomerization conditions including a temperature in a range of from 40°–235° C., a pressure of from 700 to 7000 kPa and a space velocity of from 0.1 to 10. A chloride concentration of 30 to 300 ppm is maintained in the reaction zone. The effluent from the reaction zone enters a stabilizer where it is separated into a product stream of $C_4$–$C_7$ hydrocarbons and a second gas stream which is removed from the process.

Other aspects of this invention relate to feed stream compositions, effluent stream compositions, reactor configurations, hydrogen concentrations, separation facilities and catalyst details.

DETAILED DESCRIPTION OF THE INVENTION

Figure 1:
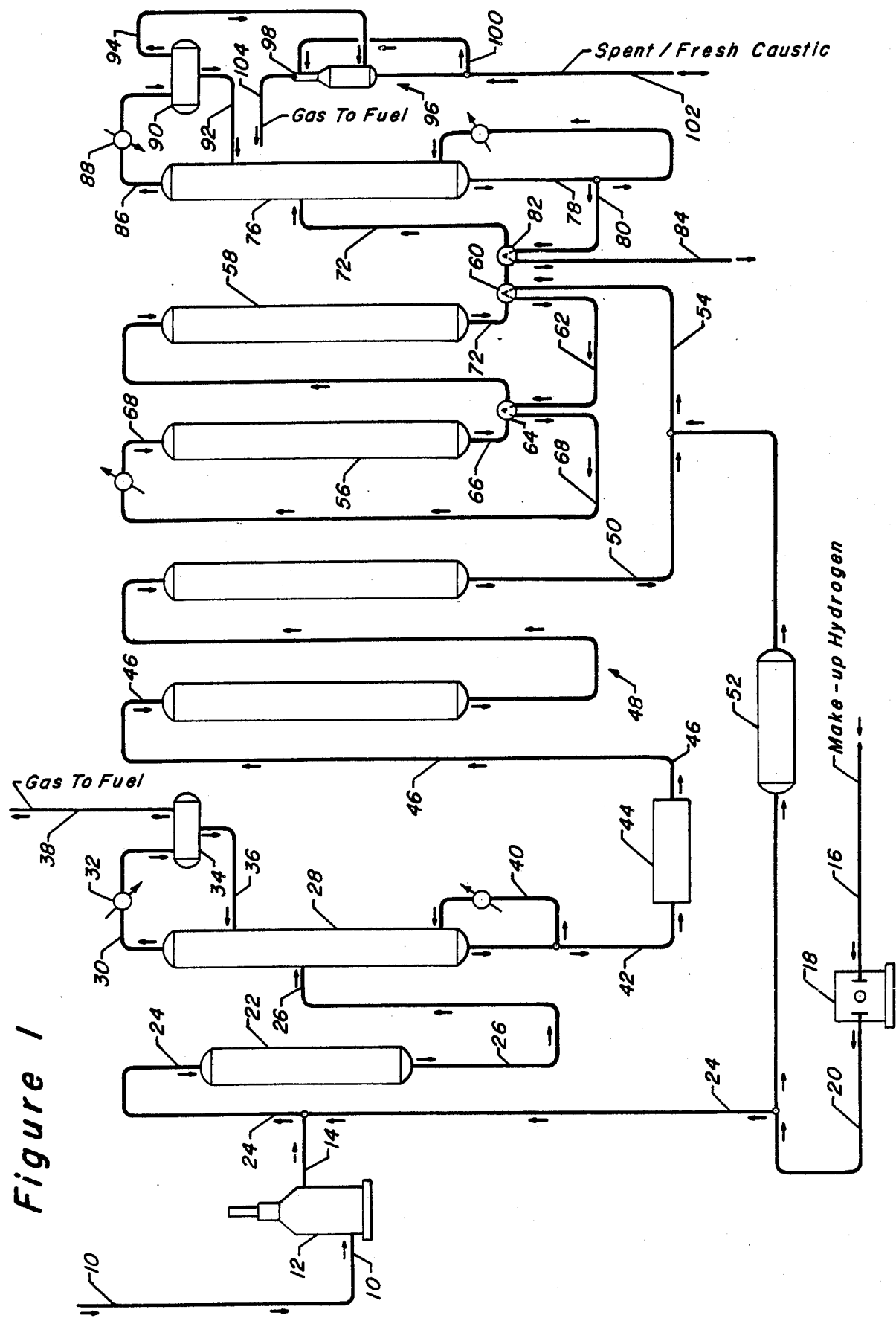
FIG. 1 is a schematic representation of a hydrotreating and isomerization process arranged in accordance with this invention.

The feedstocks that can be used in this invention include hydrocarbon fractions rich in $C_4$–$C_7$ normal paraffins. The term "rich" is defined to mean a stream having more than 50% of the mentioned component. Preferred feedstocks are substantially pure normal paraffin streams having from 4 to 6 carbon atoms or a mixture of such substantially pure normal paraffins. Other useful feedstocks include light natural gasoline, light straight run naphtha, gas oil condensate, light raffinates, light reformate, light hydrocarbons, field butanes, and straight run distillates having distillation end points of about 77° C. (170° F.) and containing substantial quantities of $C_4$–$C_6$ paraffins. The feed stream may also contain low concentrations of unsaturated hydrocarbons and hydrocarbons having more than 7 carbon atoms. The concentration of these materials should be limited to 10 wt.% for unsaturated compounds and 20 wt.% for heavier hydrocarbons in order to restrict hydrogen consumption and cracking reactions.

These feeds will usually contain sulfur and oxygen compounds which will interfere with the isomerization operations. Sulfur contaminants are present with the original crude oil fraction and include mercaptans, sulphides, disulphides and thiophenes. For light straight run feeds, sulfur concentrations will usually range from 20 to 300 ppm. Although light straight run feeds generally contain few naturally occurring oxygenate compounds, contamination from other processes can introduce significant amounts of oxygenate compounds such as alcohols, ethers, aldehydes and ketones in feedstocks. Both of these contaminants are removed by the first hydrotreatment portion of the process herein disclosed.

The feedstock is first mixed with a hydrogen containing gas stream. The gas stream should contain at least 50 wt.% of hydrogen. Preferably, the hydrogen containing gas stream will have a hydrogen concentration greater than 75 wt.% hydrogen. Hydrogen producing processes from which the gas stream is obtained can contain relatively large amounts of light hydrocarbons. These light hydrocarbons are undesirable since their presence needlessly increases the mass volume through the hydrotreater reactor and their relatively high vapor pressure can increase the loss of product in downstream separation facilities.

The gas stream is mixed with the feed in proportions that will produce a hydrogen to hydrocarbon ratio of not more than 0.9 stdm³/m³ (50 SCFB). The hydrotreatment zone of this invention can be operated with hydrogen concentrations as low as 0.18 stdm³/m³ (10 SCFB). A hydrogen concentration of 0.18 stdm³/m³ (10 SCFB) provides hydrogen for chemical demands which, require very small amounts of hydrogen for the desulfurization and deoxygenation reactions, and sufficient hydrogen partial pressure to drive the reaction. Hydrogen concentrations above 0.9 stdm³/m³ (50 SCFB) in the reaction zone interfere with the economical operation of the process.

The feed is heated and then enters a hydrotreatment reactor. Conditions within the reaction zone typically include a temperature in the range of 200°–350° C., a pressure of from 700 to 5600 kPa and a liquid hourly space velocity of from 1 to 20. Typically, the reaction conditions are selected to keep the hydrocarbon feed in a vapor phase.

The hydrotreatment reactor contains a fixed bed of hydrotreatment catalyst. Catalytic composites that can be used in this process include traditional hydrotreating catalysts. Combinations of clay and alumina-containing metallic elements from both Group VIII and Group VIB of the Periodic Table have been found to be particularly useful. Group VIII elements include iron, cobalt, nickel, ruthenium, rhenium, palladium, osmium, indium and platinum with cobalt and nickel being particularly preferred. The Group VIB metals consist of chromium, molybdenum and tungsten, with molybdenum and tungsten being particularly preferred. The metallic components are supported on a porous carrier material. The carrier material may comprise alumina, clay or silica. Particularly useful catalysts are those containing a combination of cobalt or nickel metals ranging from 2.0 to 5 wt.% and from 5 to 15 wt.% molybdenum on an alumina support. The weight percentages of the metals are calculated as though they existed in the metallic state. Typical commercial catalysts comprise spherical or extruded alumina based composites impregnated with Co-Mo or Ni-Mo in the proportions suggested above. The ABD of commercial catalysts generally range from 0.5 to 0.9 g/cc with surface areas ranging from 150 to 250 m$^2$/g. Generally, the higher the metals content on the catalyst, the more active the catalyst.

Effluent from the hydrotreatment reactor enters a separation zone that divides light gases from heavier hydrocarbons. The heavier hydrocarbons serve as feed to the isomerization zone. These light gases will comprise hydrogen, and hydrogen sulfide and water which are formed in the desulfurization and deoxygenation of the feed stream. Additional light gases can include $C_1$–$C_3$ hydrocarbons which may have entered with the feed or were produced by a minor degree of hydrocracking. The separator is typically a trayed column having from 15 to 30 trays. Hydrogen and other light gases are recovered as an overhead from the reflux system of the separator. Net overhead gases from the separator are removed from the process and usually used as fuel.

In the absence of any recycle system, it is important to minimize the loss of isomerizable hydrocarbons with the net gas. The loss of isomerizable hydrocarbons is reduced by the limited hydrogen concentration in the hydrotreater reactor which lowers the volume of the net overhead gas. When the hydrogen concentration to the hydrotreatment zone is limited, it has been found that isomerizable hydrocarbons losses of less than 0.5 wt.% can be obtained with a ratio of reflux to separator feed between 0.05 and 0.5. When processing feeds composed of primarily of $C_5$ and higher paraffins, a reflux to feed ratio is usually between 0.1 to 0.2. If the process is used for the production of a $C_5$+ isomerate product, the separator may further minimize the loss of isomerizable hydrocarbons by concentrating $C_4$ hydrocarbons in the reflux loop. In this manner, a small amount of $C_4$ hydrocarbons, in separator feed, as little as 1 to 2% can enrich the reflux to the column. This enriched reflux displaces the $C_5$ hydrocarbons from the overhead which would otherwise escape with the net gas.

A desulfurized and deoxygenated hydrocarbon stream passes out of the separator. The hydrotreatment process, in normal operation, will reduce sulfurous hydrocarbons to less than 0.5 ppm and oxygenated hydrocarbons to 0.1 ppm or less. At these contaminant levels, the isomerizable hydrocarbons could be charged directly from the separator to an isomerization reaction zone. However, the isomerizable hydrocarbons are usually passed first through a sulfur guard bed and a series of feed driers. The sulfur guard bed protects the isomerization zone from temporary upsets in the operation of the hydrotreatment zone or separator that could temporarily increase the sulfur levels beyond acceptable levels. Driers are usually needed to remove water from the separator liquid. For many operations, it is impractical to reduce the water concentration in the separator liquid to less than 10 ppm. A series of driers remove substantially all of the remaining water so that both the water and oxygenated hydrocarbons are reduced to less than 0.1 ppm before the isomerizable hydrocarbons enter the isomerization zone.

Elimination of a hydrogen recycle also facilitates the use of the sulfur guard bed and driers. In traditional flow schemes recovery of hydrogen from the hydrotreater effluent for use in a hydrogen recycle system would lower the temperature of the hydrotreated feed before it entered the hydrotreater separator. The most efficient way to then raise the temperature of the hydrotreated feed to upstream of the separator was to heat-exchange it against the liquid bottoms of the separator. After heat exchanging the separator bottoms liquid against the incoming feed, it was then necessary to raise the temperature of the liquid bottoms before it entered the sulfur guard bed. Without a hydrogen recycle, the feed to separator usually has sufficient temperature to pass directly from the hydrotreater reactor to the separator, and the separator bottoms can pass directly to the sulfur guard bed without additional heat input.

After treatment and separation, the hydrogenated hydrocarbons are used as hydrocarbon feed to the isomerization zone. Hydrogen is admixed with the isomerization zone feed in an amount that will provide a hydrogen to hydrocarbon mol ratio equal to or less than 0.9 stdm$^3$/m$^3$ (50 SCFB) in the effluent from the isomerization zone. The hydrogen to hydrocarbon mol ratio of 0.9 or less at the effluent has been found to provide sufficient excess hydrogen for operation of the process. Although no net hydrogen is consumed in the isomerization reaction, the isomerization zone will have a net consumption of hydrogen often referred to as the stoichiometric hydrogen requirement which is associated with a number of side reactions that occur. These side reactions include cracking and disproportionation. Other reactions that will also consume hydrogen include olefin and aromatics saturation. For feeds having a low level of unsaturates, satisfying the stoichiometric hydrogen requirements demand a hydrogen to hydrocarbon ratio for the inlet stream of between 0.5 to 1.8 stdm$^3$/m$^3$ (30 to 100 SCFB). Hydrogen in excess of the stoichiometric amounts for the side reactions is maintained in the reaction zone to provide good stability and conversion by compensating for variations in feed stream compositions that alter the stoichiometric hydrogen requirements and to prolong catalyst life by suppressing these side reactions. If left unchecked, the side reactions reduce conversion and lead to the formation of carbonaceous compounds, usually referred to as coke, that foul the catalyst. It has now been found that the amount of hydrogen needed for suppressing coke formation need not exceed dissolved hydrogen levels. The amount of hydrogen in solution at the normal conditions of the isomerization zone effluent will usually be in a ratio of from about 0.35 stdm$^3$/m$^3$ (20 SCFB) to less than 0.2 stdm$^3$/m$^3$ (10 SCFB). The amount of excess hydrogen over the stoichiometric requirements that is required for good stability and conversion is in a ratio of hydrogen to hydrocarbons of from 0.2 to less than 0.9 stdm$^3$/m$^3$ as measured at the effluent of the isomerization zone. Adding the dissolved and excess hydrogen proportions show that a ratio 0.9 stdm$^3$ hydrogen to m$^3$ hydrocarbon at the effluent will satisfy the hydrogen requirements for most feeds. When the hydrogen to hydrocarbon ratio exceeds 0.9, it is not economically desirable to operate the isomerization process without the recycle of hydrogen to the isomerization zone for the reasons given previously due to the previously described product losses.

Hydrogen may be added to ether feed mixture in any manner that provides the necessary control for the addition of small hydrogen quantities. Metering and monitoring devices for this purpose are well known by those skilled in the art. As currently practiced, a control valve is used to meter the addition of hydrogen to the feed mixture. The hydrogen concentration in the outlet stream or one of the outlet season fractions is monitored by a hydrogen monitor and the control valve setting position is adjusted to maintain the desired hydrogen concentration. The direct effluent from the isomerization reaction zone contains a relatively high concentration of chlorides that can attack metal components of the monitor. Thus, the monitor preferably measures the concentration of hydrogen in a stream from the isomerization zone that has undergone caustic treatment for chloride removal such as a stabilizer off gas stream. Nevertheless, the hydrogen concentration at the effluent is calculated on the basis of total effluent flow rates.

The hydrogen and isomerization zone feed mixture is contacted in the reaction zone with an isomerization catalyst. The isomerization catalyst consists of a high chloride catalyst on an aluminum base containing platinum. The aluminum is an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt.% of the platinum. Other platinum group metals may be present in a concentration of from 0.1 to 0.25 wt.%. The platinum component may exist within the final catalytic composite as an oxide or halide or as an elemental metal. The presence of the platinum component in its reduced state has been found most suitable for this process.

The catalyst also contains a chloride component. The chloride component termed in the art "a combined chloride" is present in an amount from about 2 to about 10 wt.% based upon the dry support material. The use of chloride in amounts greater than 5 wt.% have been found to be the most beneficial for this process.

There are a variety of ways for preparing the catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-aluminum catalyst base. An alternate method of increasing the halogen concentration in the final catalyst composite is to use an aluminum hydrosol to form the aluminum carrier material such that the carrier material also contains at least a portion of the halogen. Halogen may also be added to the carrier material by contacting the calcined carrier material with an aqueous solution of the halogen acid such as hydrogen chloride, hydrogen fluoride, or hydrogen bromide.

It is generally known that high chlorided platinum-alumina catalysts of this type are highly sensitive to sulfur and oxygen-containing compounds. For this reason, the sulfur concentration of 0.5 ppm or less is required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. The more stringent limitation on water and oxygenate compounds that decompose to form water stems from the fact that water can act to permanently deactivate the catalyst by removing high activity chloride from the catalyst and replacing it with inactive aluminum hydroxide.

Operating conditions within the isomerization zone are selected to maximize the production of isoalkane product from the feed components. Temperatures within the reaction zone will usually range from about 40°–235° C. (100°–455° F.). Lower reaction temperatures are generally preferred since they usually favor equilibrium mixtures of isoalkanes versus normal alkanes. Lower temperatures are particularly useful in processing feeds composed of $C_5$ and $C_6$ alkanes where the lower temperatures favor equilibrium mixtures having the highest concentration of the most branched isoalkanes. When the feed mixture is primarily $C_5$ and $C_6$ alkanes temperatures in the range of from 60°–160° C. are preferred. When it is desired to isomerize significant amounts of $C_4$ hydrocarbons, higher reaction temperatures are required to maintain catalyst activity. Thus, when the feed mixture contains significant portions of $C_4$–$C_6$ alkanes most suitable operating temperatures are in the range from 145°–225° C. The reaction zone may be maintained over a wide range of pressures. Pressure conditions in the isomerization of $C_4$–$C_6$ paraffins range from 700 to 7000 kPa. Preferred pressures for this process are in the range of from 2,000 to 3,000 kPa. The feed rate to the reaction zone can also vary over a wide range. These conditions include liquid hourly space velocities ranging from 0.5 to 12 hr.$^{-1}$, however, space velocities between 1 and 6 hr.$^{-1}$ are preferred.

Operation of the reaction zone also requires the presence of a small amount of an organic chloride promoter. The organic chloride promoter serves to maintain a high level of active chloride on the catalyst as low levels are continuously stripped off the catalyst by the hydrocarbon feed. The concentration of promoter in the reaction zone is maintained at from 30 to 300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

A more complete understanding of the process may be obtained from FIG. 1 which schematically shows the major piping and equipment items for a particular embodiment of the process (Pumps, compressor, instruments and other such equipment has been eliminated where not necessary for an understanding of the process). A hydrocarbon feed made up primarily of $C_4$–$C_7$ hydrocarbons is pumped into a heater 12 via feed line 10. Heater 12 raises the temperature of the feed to hydrotreatment temperature. The feed leaves the heater via line 14. A compressor 18 raises the pressure of a hydrogen rich stream carried by line 16 and supplies hydrogen to both the hydrotreatment and isomerization zones via line 20. Hydrogen from line 20 is admixed with feed from line 14 and enters a hydrotreater reactor 22 via a line 24.

An effluent line 26 carries desulfurized and deoxygenated hydrocarbons from the hydrotreater reactor 22 to a separator which comprises a stripping column 28. Stripping column 28 separates isomerizable hydrocarbons from the light gases. Light gases are taken overhead from column 28 by a line 30 and condensed in a reflux system that includes a condenser 32, and a separation drum 34. Condensed liquid is returned to the column by a line 36 and a net gas stream, containing hydrogen, hydrogen sulfide, water and light hydrocarbon gases, is taken from the drum 34 and withdrawn from the process by line 38. Isomerizable hydrocarbons are withdrawn from a reboiler loop 40 located at the bottom of column 28.

A line 42 transfers the isomerizable hydrocarbons without further heat exchange from loop 40 to sulfur and water adsorption equipment. Isomerizable hydrocarbons from line 42 first enter a sulfur guard bed 44 comprising a nickel type adsorbent. From sulfur guard bed 44, the isomerizable hydrocarbons flow via a line 46 to a series of feed dryers 48 that use a type 4Å or 13X molecular sieve as an adsorbent to remove water from the hydrocarbon stream. The isomerizable hydrocarbons exit the dryers via a line 50 and are combined with the hydrogen from line 20 in a line 54. Upstream of line 54 the hydrogen-rich stream carried by line 20 passes through a dryer 52 to remove any traces of water. The combined isomerization feed consisting of the isomerizable hydrocarbon stream and the hydrogen rich stream are passed to the isomerization reaction zone via line 54.

The figure shows a two-reactor system in the isomerization zone comprising a first stage reactor 56 and a second stage reactor 58. The catalyst used in the process is distributed equally between the two reactors. It is not necessary that the reaction be carried out in two reactors but the use of two reactors confer several benefits on the process. The use of two reactors and specialized valving (not shown) allows partial replacement of the catalyst system without taking the isomerization unit off stream. For the short periods of time during which replacement of catalyst may be necessary, the entire flow of reactants may be processed through only one reaction vessel while catalyst is replaced in the other. The use of two reaction zones also aids in maintaining lower catalyst temperatures. This is accomplished by having any exothermic reaction such as hydrogenation of unsaturates performed in the first vessel 56 with the rest of the reaction carried out in a final reactor stage at more favorable temperature conditions. FIG. 1 demonstrates this type of operation where the relatively cold hydrogen and hydrocarbon feed mixture taken by line 54 is passed through a cold feed exchanger 60 that heats the incoming feed against the effluent from the final reactor 58. Line 62 carries the feed from the cold feed exchanger to a hot feed exchanger 64 where the feed is heated against the effluent from the first reactor 56. Line 68 carries the partially heated feed from hot feed exchanger 64 through an inlet exchanger 70 that supplies any additional heat requirements for the fedd and then into the first reactor 56. Effluent from first reactor 56 is carried to the second reactor 58 by a line 66 after passage through exchanger 64 as previously described. Line 72 carries the isomerization zone effluent from second reactor 58 through cold feed exchanger 60 as previously described and into separation facilities.

At minimum, the separation facilities divide the reaction zone effluent into a product stream comprising $C_4$ and heavier hydrocarbons and a gas stream which is made up of lighter hydrocarbons and hydrogen. Suitable designs for rectification columns and separator vessels are well known to those skilled in the art. The separation section may also include facilities for recovery of normal alkanes. Normal alkanes recovered from the separation facilities may be recycled to the isomerization reaction zone to increase the conversion of normal alkanes to isoalkanes. Line 72 carries the effluent from second reactor 58 to a stabilizer column 76. Stabilizer column 76 is operated to deliver a bottoms fraction containing $C_4$ and heavier hydrocarbons and an overhead fraction of $C_3$ hydrocarbons and lighter boiling compounds. The stabilizer column includes a reboiler loop 78 from which the $C_4+$ product stream is withdrawn by line 80. Products taken by line 80 pass through a product exchanger 82 that heats the reactor effluent before it enters column 76. Cooled product is recovered from exchanger 82 via product line 84. $C_3$ and lighter hydrocarbons and any excess hydrogen from the reaction zone are taken overhead from stabilizer column 76 through line 86, cooled in condenser 88 and separated into a gas stream and reflux by separator drum 90. Line 92 returns reflux from vessel 90 to the top of column 76 and line 94 carries the net gas from separator drum 90 to scrubber section 96.

Scrubber section 96 contacts gas from drum 90 with a suitable treatment solution for neutralizing and/or removing acidic components that may have originated with the chloride addition to the isomerization zone and may be present in the gas stream. Typically, the treatment solution will be a caustic that is pumped around a contacting vessel 98 in a loop 100. Spent caustic is withdrawn and fresh caustic is added to the scrubber section by a line 102. After treatment in the scrubber section 96, the net gas is removed from the process via line 104. Gas recovered by line 104 will usually be put to use as a fuel.

The process of this invention is characterized by high conversion and high selectivity.

The following examples were prepared to show that the process of this invention can operate effectively at the low hydrogen levels used in both the hydrotreating and isomerization sections.

EXAMPLE I

In this example, a hydrocarbon feed having the composition labeled "A" in Table 1 was charged to a hydrotreatment reactor. Before entering the reactor, hydrogen was admixed with the hydrocarbon feed in an amount that produced a total hydrogen concentration of 0.88 stdm$^3$/m$^3$. The reaction zone contained an alumina catalyst having approximately 3.5 wt.% cobalt and 12.0 wt.% molybdenum. The catalyst was typically formed by the following method. Powdered Kaiser and Catapal alumina, ammonium molybdate and cobalt carbonate were admixed for 1½ hours in a conical blender then charged to a paddle mixer. A solution of water and nitric acid was metered continuously to the mixer to produce a dough of uniform consistency. From the mixer, the dough was extruded through a die to produce strands of extrudate. The extrudate was calcined for one hour at 650° and two hours at 1100° F. The catalyst carrier was impregnated by an evaporative method with cobalt nitrate and ammonium molybdate. The selected metals were dissolved in a basic aqueous solution. A rotary evaporator was loaded with the catalyst carrier and then with the metal-containing solution. The excess solution was removed by conventional evaporative techniques. The dried composite was thereafter exposed to an oxidizing atmosphere using a belt calciner and a two zone oxidation. In the first zone, oxidation temperature was 625° F. The duration of the first zone oxidation was one hour. The second zone oxidation temperature was 950° F. The duration of the second zone oxidation was two hours. Typical finished catalyst promoter levels were 12 wt.% molybdenum and 3.5 wt.% cobalt.

Figure 2:
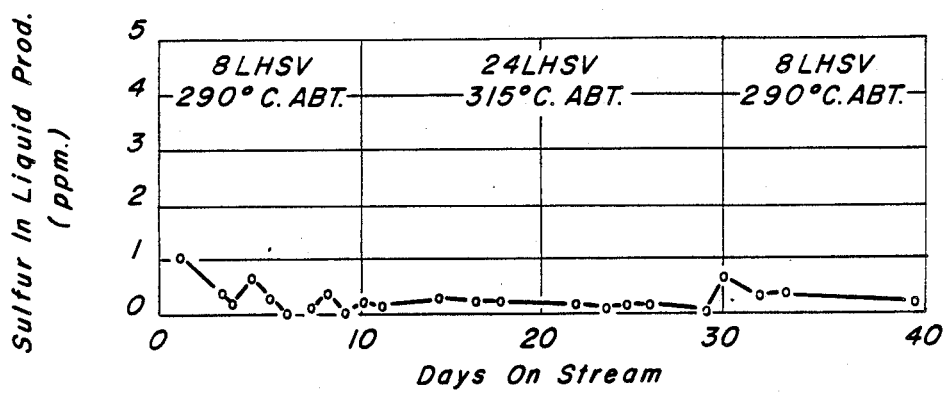
FIG. 2 is a plot of data points demonstrating the ability of the catalyst of this invention to remove sulfur at low hydrogen to hydrocarbon ratios.

Throughout this experiment, the reactor pressure was held at about 2400 kPa while the average bed temperature of the reactor was varied between 290° and 315° C. and the reactor throughout varied between 8 and 24 LHSV. Results, as demonstrated by FIG. 2, show that the average sulfur concentration in the effluent from the hydrotreatment reactor was well below the target of 0.5 ppm.

TABLE 1

| Feed Compositions in Wt. % | A | B (Run 167) | C (Run 169) |
|---|---|---|---|
| $iC_4$ | 0.1 | | 0.0 |
| $nC_4$ | 1.2 | | 1.2 |
| $iC_5$ | 3.5 | | 19.7 |
| $nC_5$ | 34.2 | | 24.2 |
| CP | 0.8 | | 2.3 |
| 2,2-DMB | 0.1 | | 0.5 |
| 2,3-DMB | 0.4 | | 1.4 |
| 2 MP | 3.2 | | 10.4 |
| 3 MP | 2.3 | 4.5 | 6.4 |
| $nC_6$ | 37.8 | 95.5 | 17.1 |
| MCP | 4.2 | | 7.8 |
| CH | 2.2 | | 3.8 |
| Benzene | 1.9 | | 4.1 |
| $C_7+$ | 8.1 | | 1.1 |
| ppm S | 150 | 200 | 260 |

EXAMPLE II

In this example, several different feeds were used to test the deoxygenation capability of this invention at different hydrogen concentrations and with different oxygenate contaminants. Table 2 shows the results of these experiments. The feed streams under consideration are those described in Table 1 and indicated by letter in Table 2. Each feed stream was admixed with hydrogen until it contained the concentration listed in Table 2. Oxygenate contaminants were introduced by spiking the feed with either methyl tertiary butyl ether (MTBE) or methanol to the concentration listed in Table 2. After contact with the same catalyst, as used in Example I at a pressure of 2410 kPa (350 psi) and a 8 LHSV, very good deoxygenation results were obtained at average bed temperatures ranging from 290°–315° C. Table 2 shows that very low oxygenate levels were obtained with the low hydrogen concentrations of this invention. Moreover, the degree of deoxygenation removal was comparable to that obtained with the higher hydrogen concentrations which typify the prior art processes.

TABLE 2

| CONDITIONS | | | CONTAMINANT | PPM | |
|---|---|---|---|---|---|
| Feed stock | $H_2$ stdm$^3$/m$^3$ | Rx. T. °C. | Compound | Feed | Product |
| (167) B | 3.5 | 315 | MTBE | 200 | .02 |
| (167) B | .88 | 315 | MTBE | 200 | .02 |
| (167) B | 3.5 | 300 | MTBE | 200 | .02 |
| (167) B | .88 | 300 | MTBE | 200 | .02 |
| (167) B | 3.5 | 315 | MeOH | 140 | .01 |
| (167) B | .88 | 315 | MeOH | 140 | .03 |
| (167) C | 3.5 | 290 | MeOH | 150 | .04 |
| (167) C | .88 | 345 | MeOH | 150 | .07 |
| (167) C | .88 | 345 | MeOH | 150 | .01 |

EXAMPLE III

Figure 3:
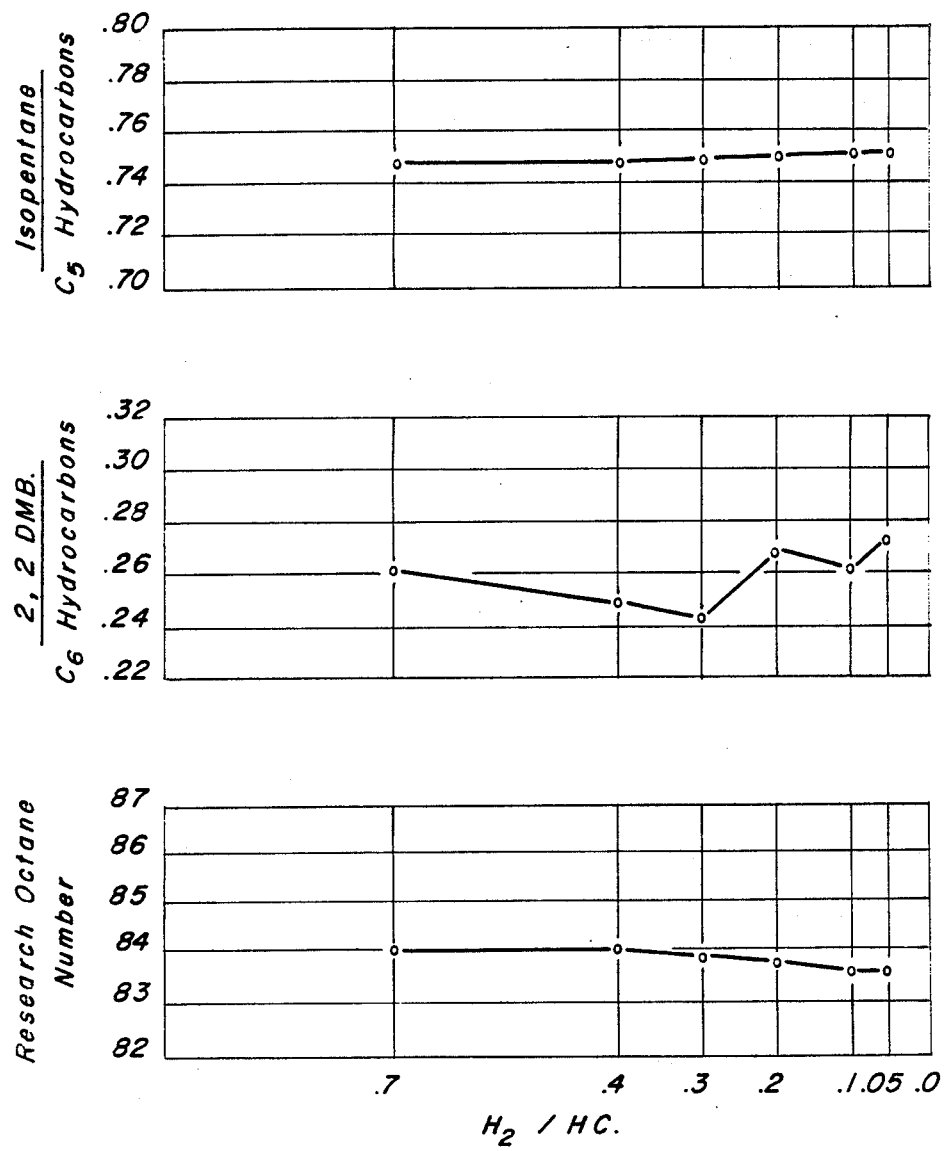
FIG. 3 contains a series of graphs showing input and output properties of the feed and effluent associated with an isomerization zone of this invention.

In this example, a hydrocarbon feed having an average composition given in Table 3 was charged to a two reactor isomerization zone of the type shown generally in FIG. 1. Before entering the reaction zone, hydrogen was admixed with the hydrocarbon feed to provide indicated hydrogen to hydrocarbon mol ratios as given in FIG. 3 and ranging from 0.7 to 0.05 at the outlet of the reaction zone which corresponds to a range of approximately 12.4 to 0.88 stdm$^3$/m$^3$. Each reaction zone contained an alumina catalyst having 0.25 wt.% platinum and 5.5 wt.% chlorine.

TABLE 3

| Composition in wt. % | Reactor Charge |
|---|---|
| sp. gr. | 0.65 |
| $iC_4$ | 0.3 |
| $nC_4$ | 4.5 |
| $iC_5$ | 25.7 |
| $nC_5$ | 25.5 |
| CP | 1.4 |
| 22DMB | 0.9 |
| 23DMB | 1.5 |
| 2MP | 9.6 |
| 3MP | 6.5 |
| $nC_6$ | 15.7 |
| MCP | 6.0 |
| BZ | 1.4 |
| CH | 0.5 |
| $C_7+$ | 0.1 |

The catalyst was prepared by vacuum impregnating an alumina base in a solution of chloroplatinic acid, 2% hydrochloric acid, and 3.5% nitric acid in a volume ratio of 9 parts solution to 10 parts base to obtain a peptized base material having a platinum to base ratio of approximately 0.9. The resulting mixture was cold-rolled for approximately 1 hour and evaporated until dry. Afterward, the catalyst was oxidized and the chloride content adjusted by contact with a 1M hydrochloric acid solution at 525° C. at a rate of 45 cc/hour for 2 hours. The catalyst was then reduced in electrolytic hydrogen at 565° C. for 1 hour and was found to contain approximately 0.25 wt.% Pt and approximately 1 wt.% chloride. Impregnation of active chloride to a level of approximately 5.5 wt.% was accomplished by sublimating aluminum chloride with hydrogen and contacting the catalyst with the sublimated aluminum chloride for approximately 45 minutes at 550° C.

The hydrocarbon feed mixture entered the first reaction zone at a temperature of approximately 160° C. The feed mixture at a temperature of approximately 175° C. was taken from the first reaction zone and, after heat exchange with the incoming feed, entered the second reaction zone at a temperature of approximately 140° C.

The exit temperature of the second reaction zone was maintained at approximately 140° C. and the feed passed through the reaction zones at a liquid hourly space velocity of about 2.4 hr.$^{-1}$. An average pressure of about 3100 kPa was maintained in both reaction zones. The effluent from the second reaction zone was recovered at a temperature of about 140° C. At the beginning of the run, the $H_2/HC$ ratio at the outlet was kept at about 0.7 which corresponds to the typical range for a low $H_2/HC$ ratio as practiced in the prior art. Over a period of several months, the $H_2/HC$ ratio was lowered to the ratio of this invention. Average values for the isopentane to $C_5$ hydrocarbon ratio, 2,2-dimethylbutane to $C_6$ hydrocarbon ratio and research octane in the effluent were plotted at selected $H_2/HC$ ratios over the course of this run. As the data shows, the process of this invention was able to maintain substantially consistent values for these parameters as the $H_2/HC$ ratio was decreased. At the time of writing this application, the reactor system had experienced over 8,000 hours of operation at a $H_2/HC$ ratio of about 0.05 without any appreciable loss of normal paraffin conversion or octane number reduction in the recovered effluent. Therefore, it has been shown that the process of this invention, using the catalyst as herein described, will provide a stable conversion of normal paraffins to isoparaffins at hydrogen addition levels that leave a ratio no more than 0.05 $H_2$ to hydrocarbon in the effluent.

What is claimed is:

1. A method of supplying hydrogen to a combined hydrotreatment and isomerization process, said method comprising:
   (a) forming a hydrotreater feed by combining a hydrocarbon feedstock comprising $C_4$–$C_7$ hydrocarbons, and including sulfur and oxygen-containing hydrocarbon compounds, with a first hydrogen containing stream to produce a hydrogen to hydrocarbon ratio of from 0.2 to 0.9 stdm$^3$/m$^3$ (10 to 50 SCFB) in said hydrotreater feed;
   (b) contacting said hydrotreater feed in a hydrotreater reactor with a catalyst comprising a Group VIB metal and a Group VIII metal on an alumina support at conditions including a temperature in the range of 200°–350° C., a pressure of from 700 to 5600 kPa and a liquid hourly space velocity of from 1 to 20 to convert said sulfur and oxygen-containing compounds to hydrocarbons, hydrogen sulfide and water;
   (c) recovering a hydrotreater effluent from said hydrotreater reactor;
   (d) passing said hydrotreater effluent to a first separator, and separating said effluent into a first gas stream comprising hydrogen, hydrogen sulfide, and water and a treated stream comprising hydrocarbons having from 4–7 carbon atoms;
   (e) rejecting said first gas stream from said process;
   (f) forming an isomerization feed by combining said treated stream with a second hydrogen-containing stream in a proportion that produces a hydrogen to hydrocarbon ratio of from 0.9 to 1.8 stdm$^3$/m$^3$ (50 to 100 SCFB);
   (g) contacting said isomerization feed in an isomerization reaction zone with an isomerization catalyst comprising alumina, having from 0.01 to 0.25 wt.% platinum and from 2 to 10 wt.% of a chloride component at isomerization conditions including a temperature in a range of from 40°–235° C., a pressure of from 700 to 7000 kPa and a space velocity of from 0.1 to 10;
   (h) maintaining a chloride concentration in said isomerization reaction zone of from 30 to 300 ppm;
   (i) recovering a second effluent stream from said isomerization reaction zone; and
   (j) separating said second effluent stream in a stabilizer column into a product stream, $C_4$–$C_7$ hydrocarbons and a second gas stream which is removed from the process.

2. The method of claim 1 wherein said second effluent comprises a $C_5$–$C_7$ product stream and said hydrocarbon feedstock includes a minimum of 1 wt.% $C_4$ hydrocarbon.

3. The method of claim 2 wherein said separator comprises a stripper column having a reflux stream comprising $C_4$ hydrocarbons.

4. The method of claim 1 wherein said treated stream passes through a sulfur guard bed before entering said isomerization reaction zone.

5. The method of claim 4 wherein said treated stream passes from said first separator into a sulfur guard bed without additional heat input.

6. The method of claim 1 wherein said first and second hydrogen containing streams originate from a common source.

7. The method of claim 1 wherein said catalyst comprises 3 to 5 wt.% cobalt, and 10 to 15 wt.% molybdenum on a gamma-alumina support.

8. A method supplying hydrogen to a combined hydrotreatment and isomerization process, said method comprising:
   (a) compressing a supply stream, rich in hydrogen, to a pressure of from 700 to 7000 kPa and splitting said gas stream into first and second hydrogen streams;
   (b) combining said first hydrogen stream with a feed stream comprising $C_4$–$C_7$ hydrocarbons, sulfurous hydrocarbons and oxygenated hydrocarbons to a hydrotreating reactor in an amount that will produce a hydrotreater feed having a hydrogen to hydrocarbon ratio of from 0.2 to 0.9 stdm$^3$/m$^3$ (10 to 50 SCFM);
   (c) contacting said hydrotreater feed in a hydrotreater reactor with a catalyst comprising a Group VIB metal and a Group VIII metal on an alumina support at conditions including a temperature in the range of 200°–350° C., a pressure of from 700 to 5600 kPa and a liquid hourly space velocity of from 1 to 20 to convert said sulfur and oxygen-containing compounds to hydrocarbons, hydrogen sulfide and water;
   (d) separating said effluent in said separator into a first overhead stream comprising hydrogen, hydrogen sulfide and water and a treated feed stream comprising hydrocarbons having from 4–7 carbon atoms;
   (e) removing said first overhead stream from said process;
   (f) forming an isomerization feed by combining said treated feed stream with said second hydrogen stream in a proportion that produces a hydrogen to hydrocarbon ratio of from 0.9 to 1.8 stdm$^3$/m$^3$ (50 to 100 SCFB);
   (g) contacting said isomerization feed in an isomerization reaction zone with an isomerization catalyst comprising alumina, having from 0.01 to 0.25 wt.% platinum and from 2 to 10 wt.% of a chloride component at isomerization conditions including a temperature in a range of from 40°–235° C., a pressure of from 700 to 7000 kPa and a space velocity of from 0.1 to 10;
(h) maintaining a chloride concentration in said isomerization reaction zone of from 30 to 300 ppm;
(i) recovering a second effluent stream from said isomerization reaction zone; and
(j) separating said second effluent stream in a stabilizer column into a product stream comprising $C_4$–$C_7$ hydrocarbons and a second gas stream which is removed from the process.

9. The method of claim 1 wherein said second effluent stream comprises hydrocarbons having from 5–7 carbon atoms; said hydrocarbon feedstock includes at least 2 wt.% of a $C_4$ hydrocarbon, and said first separator column has a reflux stream consisting essentially of $C_4$ hydrocarbons.

10. The process of claim 9 wherein said bottoms stream passes without heat input, from said first separator column into a sulfur guard bed before entering said isomerization reaction zone.

11. The method of claim 10 wherein said bottoms stream passes without heat input, from first separator column into a sulfur guard bed before entering said isomerization reaction zone.

* * * * *